United States Patent [19]

Haber

[11] Patent Number: 4,587,954
[45] Date of Patent: May 13, 1986

[54] ELASTOMERIC PROSTHETIC SPHINCTER

[75] Inventor: Terry M. Haber, Lake Forest, Calif.

[73] Assignee: Habley Medical Technology Corporation, Laguna Hills, Calif.

[21] Appl. No.: 574,596

[22] Filed: Jan. 27, 1984

Related U.S. Application Data

[63] Continuation-in-part of Ser. No. 566,486, Dec. 29, 1983, Pat. No. 4,552,128.

[51] Int. Cl.$^4$ ............................................. A61B 19/00
[52] U.S. Cl. ............................ 128/1 R; 128/DIG. 25; 604/247; 251/342
[58] Field of Search ................... 128/1 R, 346, D25; 251/415, 7, 75; 604/247

[56] References Cited

U.S. PATENT DOCUMENTS

| | | | |
|---|---|---|---|
| 274,447 | 3/1883 | Kennish | 604/247 |
| 2,521,426 | 3/1944 | Heaton | 24/519 |
| 2,533,924 | 12/1950 | Foley | 128/D25 |
| 3,758,073 | 10/1971 | Shulte | 251/342 |
| 3,788,327 | 1/1974 | Donowitz et al. | 604/247 |
| 3,903,894 | 9/1975 | Rosen et al. | 251/5 |
| 3,926,175 | 12/1975 | Allen et al. | 128/D25 |
| 4,224,934 | 9/1980 | Scott et al. | 128/79 |
| 4,340,061 | 7/1982 | Kees, Jr. et al. | 128/346 |
| 4,428,365 | 1/1984 | Hakky | 128/D25 |

Primary Examiner—Dalton L. Truluck
Assistant Examiner—Karen Kaechele
Attorney, Agent, or Firm—Morland C. Fischer

[57] ABSTRACT

An elastomechanical sphincter comprising a prosthetic device for implantation about a patient's lumen such as the urethra for occluding or relaxing the lumen for the treatment of incontinence. The prosthetic sphincter includes a body of elastomeric polymer material configured to define an articulating structure having a normally closed elongated occlusion orifice arranged to embrace the patient's urethra with minimal ischemic interruption of circulatory blood flow. In a first sphincter embodiment, an integrally formed manually manipulable pressure relief cuff extends from a peripheral portion of the articulating structure in such a manner that physical pulling on the pressure relief cuff in a direction transverse to the elongation of the occlusion orifice will open the orifice and thereby open the lumen. The natural elasticity of the device results in occlusion of the lumen upon releasing of the pressure relief cuff. In a second sphincter embodiment, the articulating structure includes a hollow chamber formed therein which is adapted to receive a fluid under pressure from an associated fluid reservoir. As the chamber is filled, the articulating structure expands, such that the occlusion orifice thereof applies a corresponding pressure to occlude the patient's lumen. A pressure relief disk is provided which may be manually operated to permit fluid to be transferred from the chamber to thereby reduce the occlusive pressures being applied by the occlusion orifice, whereby to permit an opening of the patient's lumen thus maximizing the movement of material (e.g. blood) therethrough.

10 Claims, 30 Drawing Figures

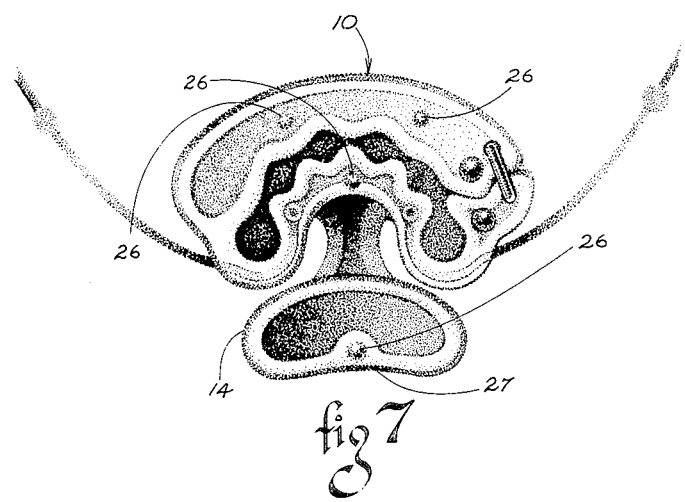
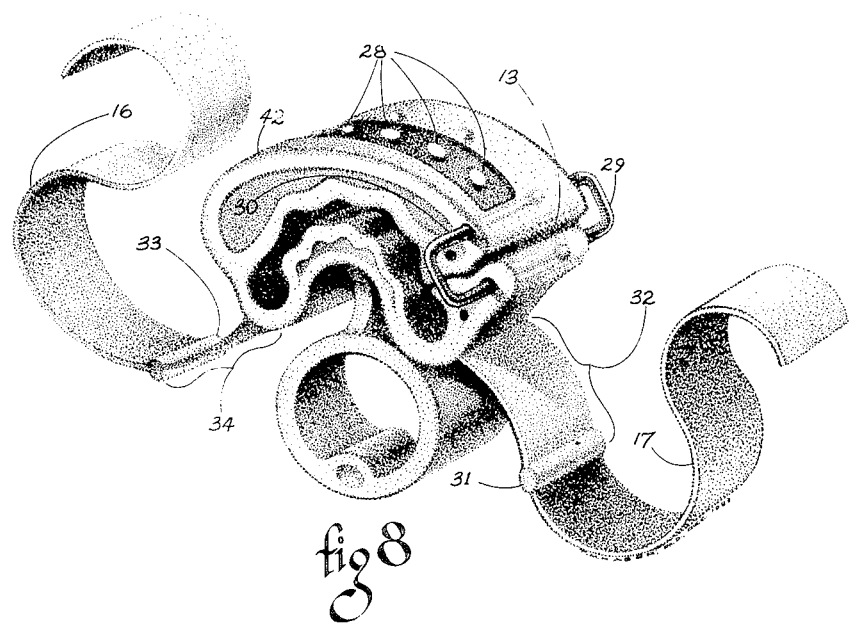
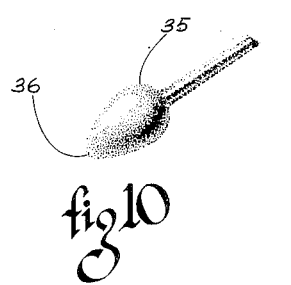
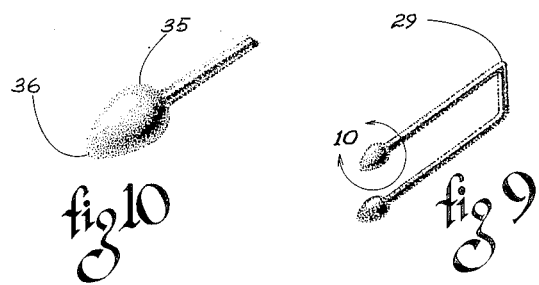

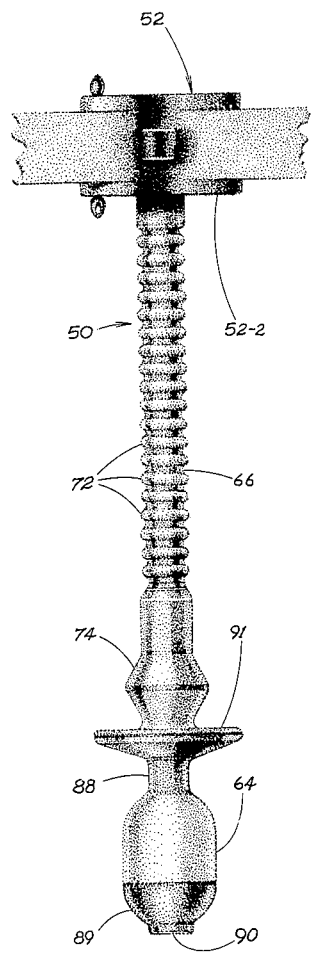
fig 11
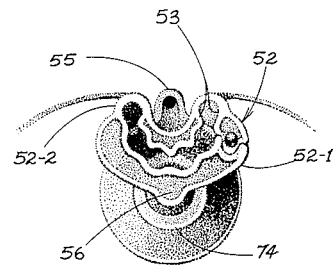
fig 12
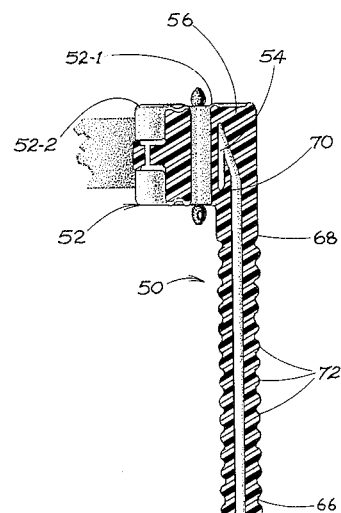
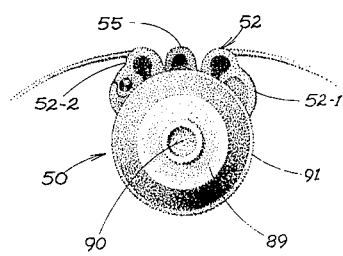
fig 13
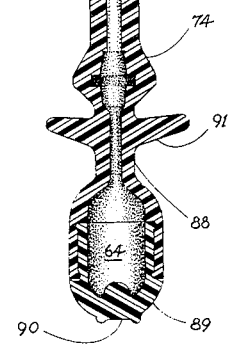
fig 14

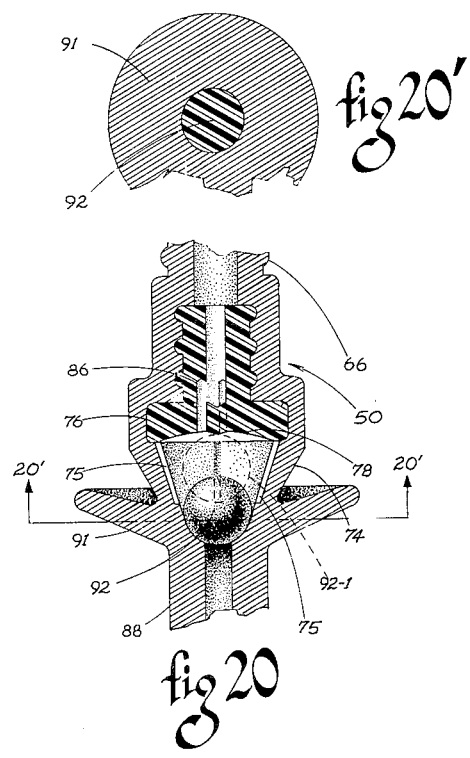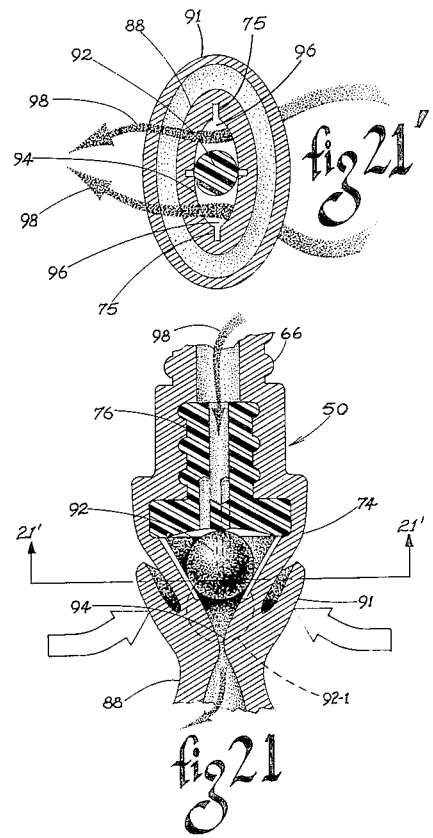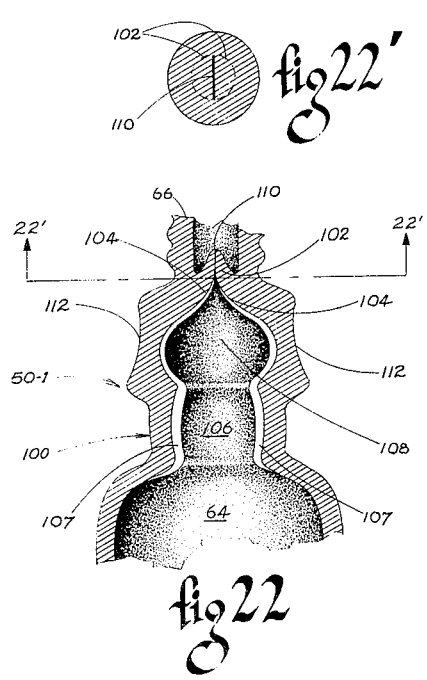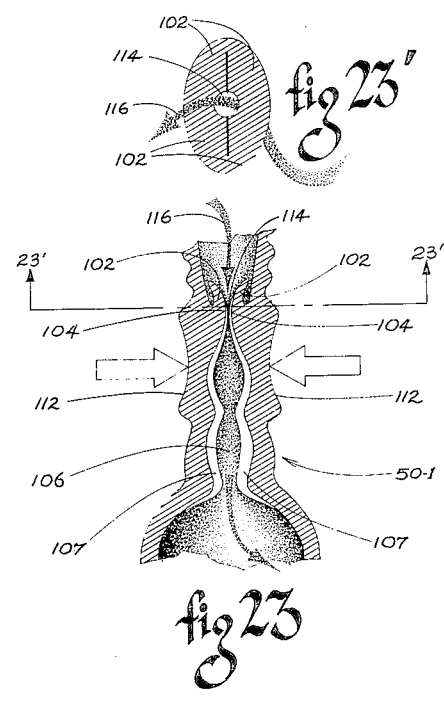

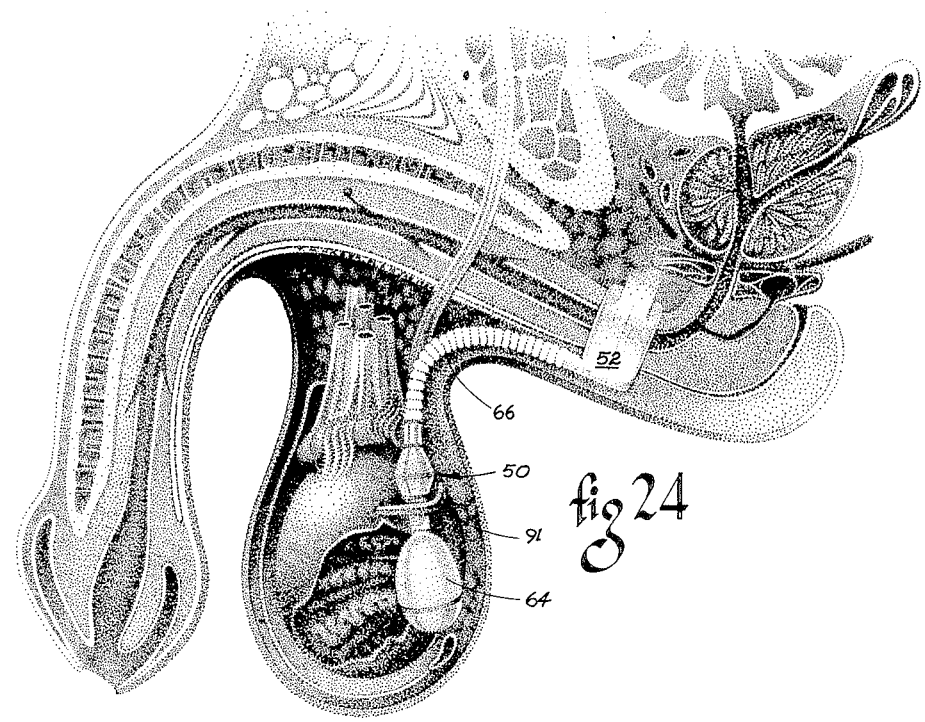
fig 24
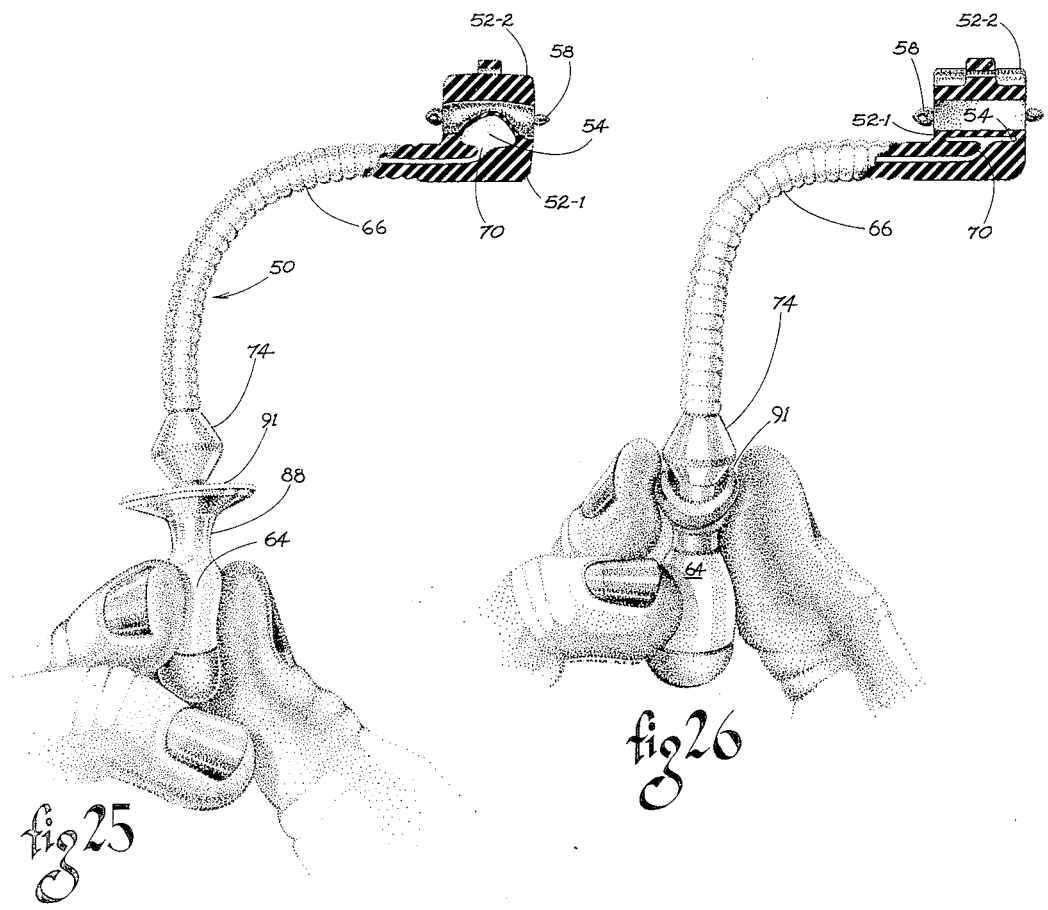
fig 25
fig 26

ELASTOMERIC PROSTHETIC SPHINCTER

CROSS REFERENCES TO RELATED PATENT APPLICATIONS

This application is a continuation-in-part of my copending patent application Ser. No. 566,486 filed Dec. 29, 1983 now U.S. Pat. No. 4,552,128.

FIELD OF THE INVENTION

This invention relates generally to prosthetic devices and, more particularly, to an elastomechanical sphincter for implantation in a patient to overcome the problem of incontinence.

BACKGROUND OF THE INVENTION

In my U.S. Pat. No. 4,401,107 entitled INTESTINAL CONTROL VALVE there is described a Gastrointestinal Sphincter which can be surgically implanted without invading the intestine itself. While the valve disclosed is primarily designed to achieve continence within the distal intestine of a patient, it could also be used in a smaller version to achieve continence within the urethra.

In my later filed copending patent application Ser. No. 435,761 entitled PROSTHETIC SPHINCTER, there is disclosed an improved closure divice in the form of an artificial sphincter wherein there is no need for any type of electrical drive motor. Rather, a flexible force-applying means is utilized to actuate the device from a remote location.

In my more recent copending patent application Ser. No. 522,107 entitled MECHANICAL PROSTHETIC SPHINCTER, there is shown a further closure device which can occlude and articulate the distal intestine, the urethra, or other such lumen, where no electrical power at all is necessary but rather the device is wholly mechanically operated. In this respect, a flexible force-applying means is used so that the actuating coponent can be located at an accessible position relative to the sphincter occlusion element itself.

Along the line of the aforementioned constructions, it is also desirable to provide an improvement in the construction of a prosthetic sphincter capable of articulating and occluding a lumen, such as the urethra, utilizing a decreased number of components than has been thought necessary heretofore.

SUMMARY OF THE INVENTION

The present invention contemplates an improved prosthetic sphincter, herein termed an "ELASTOMECHANICAL SPHINCTER," particularly useful in articulating a lumen (e.g. urethra) wherein pneumatic or hydraulic mediums, tubing which may be pron to kinks and leaks, mechanical connecting cables, electrically-driven motors and the like, as have characterized prior devices, are wholly eliminated. Also the mechanical strangulation of blood flow within the lumen, resulting in ischemic necrosis tissue and/or erosion, is vastly minimized or eliminated by virtue of the inherent flexibility of the elastomechanical sphincter.

More particularly, and in accordance with a first preferred embodiment of the invention, the present sphincter comprises a body of elastomeric polymer material configured to define an articulating structure having a normally closed, elongated occlusion orifice for surrounding a lumen such as the urethra. An integrally formed manually manipulable, pressure relief cuff extends from a peripheral portion of the articulating structure. Appropriate suture attachment means are provided to secure spaced peripheral areas of the articulating structure to adjacent bone or tissue structure in a patient such that the articulating structure can surround and gently embrace the urethra with the pressure relief cuff protruding against a palpable loose skin area of the patient. The arrangement is such that the patient can manually grasp the pressure relief cuff by compressing the skin on either side of the cuff and then pulling the cuff away from the articulating structure in a direction transverse to the elongated occlusion orifice so that the occlusion orifice opens and, in turn, permits the urethra to open. Releasing of the pressure relief cuff to its natural orientation results in automatic closing of the occlusion orifice about the urethra.

In accordance with a second preferred embodiment of the invention, the articulating structure includes a hollow chamber which is adapted to receive a fluid under pressure from a fluid reservoir. The hollow chamber communicates with the reservoir by way of a fluid channel which extends therebetween. A valve is located within the channel to control the flow of fluid between the reservoir and the articulating structure. As the chamber is filled with fluid, the articulating structure expands such that the occlusion orifice thereof closes, whereby to apply a correspondingly increased occlusive pressure to close the urethra and inhibit the movement of material therethrough. A pressure relief disk is provided which may be manually operated to relax the valve and permit fluid to transfer from the chamber of the articulating structure to the fluid reservoir. Therefore, the chamber will shrink to cause an opening of the occlusion orifice and a corresponding reduction in the occlusive pressures being applied to the urethra, so as to maximize the movement of blood and/or other materials therethrough. The present sphincter embodiment may also be located adjacent to a palpable loose skin area (e.g. at the posterior superior aspect of the scrotum) of the patient so as to minimize discomfort while allowing convenient manipulation of the sphincter and the pressure relief disk thereof.

BRIEF DESCRIPTION OF THE DRAWINGS

A better understanding of this invention will be had by now referring to the accompanying drawings in which:

FIG. 7 is another front elevational view of the elastomechanical sphincter of the first embodiment in its closed position showing a modified configuration;

FIG. 8 is a perspective view of the sphincter of FIG. 7 useful in explaining attachment means used in securing the sphincter in place about a lumen;

FIG. 9 is a perspective view of a closure staple utilized in the embodiment of FIG. 8;

FIG. 10 shows a portion of the closure staple of FIG. 9 encircled within the circular arrow 10;

FIG. 11 is an elevational view of the elastomechanical sphincter which forms the second embodiment of this invention;

FIG. 12 is an end view taken from the proximal end of the sphincter of FIG. 11;

FIG. 13 is an end view taken from the distal end of the sphincter of FIG. 11;

FIG. 14 is a cross section of the sphincter of FIG. 11;

FIG. 20 shows a detail of a normally closed flow control valve used in the sphincter embodiment of FIG. 11;

FIG. 20' is a cross section taken in the direction of arrows 20'—20' of FIG. 20;

FIG. 21 is a cross section of the valve of FIG. 20 in an opened condition;

FIG. 21' is a cross section taken in the direction of arrows 21'—21' of FIG. 21;

FIG. 22 is a cross section of an alternate pressure regulating chamber having a normally closed flow control valve body for use in the second sphincter embodiment of FIG. 11;

FIG. 22' is a cross section taken in the direction of arrows 22'—22' of FIG. 22;

FIG. 23 is a cross section of the pressure regulating chamber of FIG. 22 with the valve body thereof in an opened condition;

FIG. 23' is a cross section taken in the direction of arrows 23'—23' of FIG. 23;

FIG. 24 is a broken away anatomical view of a patient's urethra with the sphincter embodiment of FIG. 11 secured in place;

FIG. 25 is a perspective view showing the manual compression of a reservoir of the sphincter of FIG. 11 for increasing the occlusive pressures about a patient's lumen; and FIG. 26 is a perspective view showing the manual operation of a pressure relief disk of the sphincter of FIG. 11 for reducing the occlusive pressures about a patient's lumen.

DETAILED DESCRIPTION OF THE PREFERRED EMBODIMENT

Figure 1:
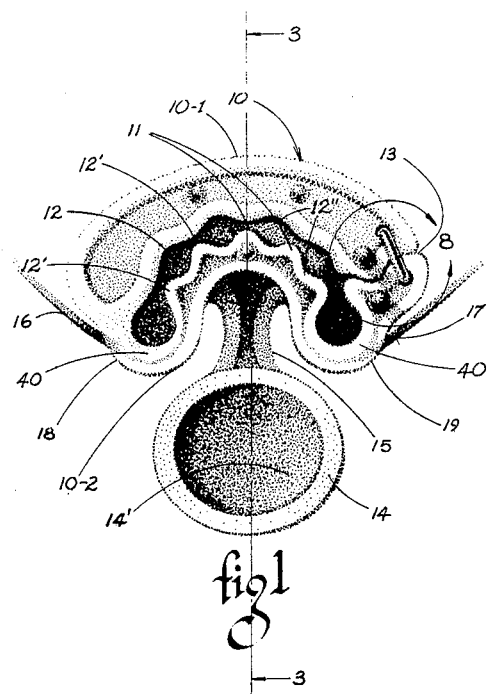
FIG. 1 is a front elevational view of the elastomechanical sphincter which forms the first embodiment of this invention showing the same in its normal closed condition about a patient's urethra.
Figure 2:
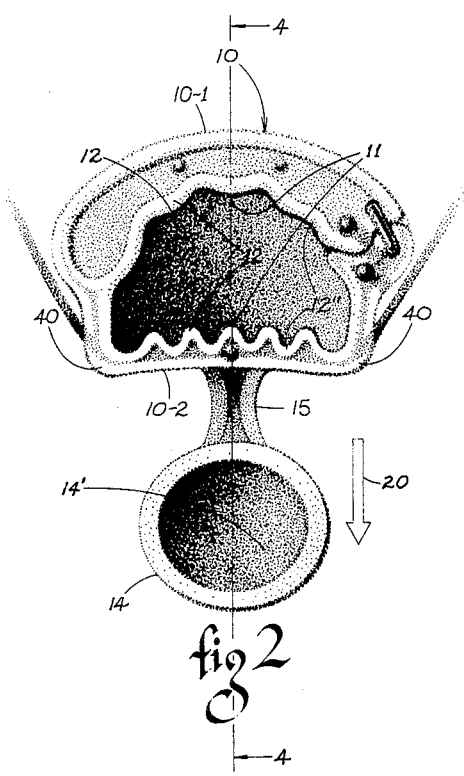
FIG. 2 is a view similar to FIG. 1 but illustrating the relative positions of parts of the device when in open condition to unblock the urethra.

Referring to FIGS. 1 through 4, and according to a first embodiment of the present invention, the elastomechanical sphincter includes a body of elastomeric polymer material, such as silicone or the like, having a spring-like memory and being shaped to define an articulating structure 10. As is best shown in FIGS. 1 and 2, the articulating structure 10 comprises upper and lower halves 10-1 and 10-2 hingedly connected together by oppositely disposed and coextensively formed hinges 40. Hinges 40 are arcuately shaped (rather than point hinges) so as to better distribute, and thereby minimize, bending and deflection forces associated with opening and closing the articulating structure, whereby to maximize the life expectancy of the disclosed sphincter and minimize any compression setting thereof. The upper and lower articulating halves 10-1 and 10-2 are arranged (in the closed position of FIG. 1) in substantially parallel alignment and adapted for reciprocal movement relative to one another whereby to selectively control the flow of material therebetween. Because of the reciprocal movement of articulating structure halves 10-1 and 10-2 in a single plane, the articulating structure 10 may be advantageously characterized as a minimal friction-inducing device, so as to minimize any possibility of tissue erosion due to ischemic necrosis. The articulating structure 10 has a normally closed elongated occlusion orifice 11 for surrounding a lumen 12. In the particular embodiment to be described, the lumen 12 constitutes a patient's urethra. However, it is also to be understood that the presently disclosed articulating structure 10 is also applicable to a lumen which is the intestine, the esophagus, a vein, an artery or the vas deferins.

A series of alternating pressure concentrating ridges 12' and pressure relief troughs 12" extend from articulating structure 10 around the periphery of the occlusion orifice 11. The pressure concentrating ridges 12' transmit occlusive forces from the articulating structure 10 to the lumen 12 to close the lumen 12. The pressure relief troughs 12" minimize the occlusion of axial blood vessels supplying the lumen 12 by providing paths of relatively lower barometric pressure extending longitudinally through articulating structure 10 so as to maximize freedom of arteriovascular blood flow and thereby minimize any possibility of ischemic erosion to the delicate tissues.

In order to position the occlusion orifice about the patient's urethra, the articulating structure 10 includes a channel 13 extending from an exterior surface into the occlusion orifice 11. This channel 13 permits spreading of the articulating structure to enable the occlusion orifice to embrace the urethra. The manner in which the channel is secured together after implantation and positioning of the device about the urethra will be described subsequently.

Figure 3:
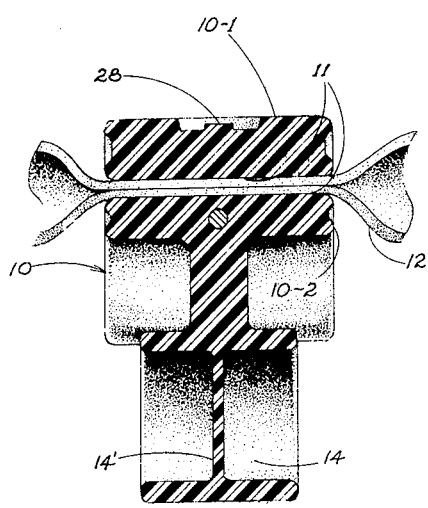
FIG. 3 is a cross section taken in the direction of the arrows 3—3 of FIG. 1.
Figure 4:
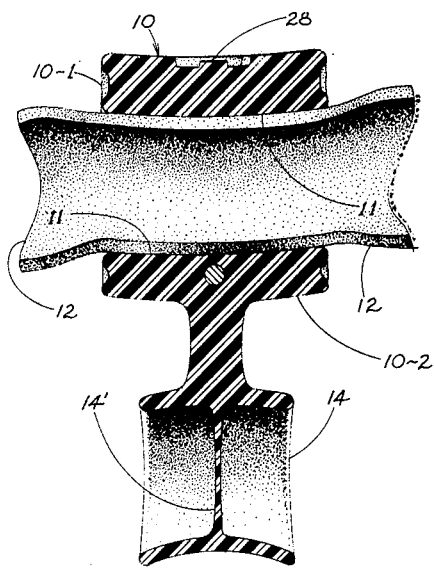
FIG. 4 is a cross section taken in the direction of the arrows 4—4 of FIG. 2.

Referring to the lower portion of FIG. 1, the articulating structure further includes a flexible and integrally formed manually manipulable pressure relief cuff 14 extending from a peripheral portion of the articulating structure as by integral extension portion 15. Pressure relief cuff 14, as shown, is preferably elliptically ring-shaped and may be provided with a supporting membrane 14', lying in the plane of the ring-shape midway between opposite sides of the ring as best shown in FIG. 3. Supporting membrane 14' allows a flexible compression of relief cuff 14 while providing transverse support therefor.

In order to secure the sphincter in place, there are provided suture attachment means 16 and 17 secured to spaced peripheral areas 18 and 19 of articulating structure 10. Means 16 and 17 extend away from the articulating structure for suitable connection to adjacent bone or tissue structure in a patient, such as the ischium of the pelvis or the crura of the penis.

FIG. 2 illustrates the contorted position of the articulating structure 10 when the pressure relief cuff 14 has been pulled downwardly in the direction of the arrow 20; that is, in a direction transverse to the elongated occlusion orifice. As will be clear from both FIGS. 2 and 4, pulling downwardly on the cuff 14 serves to open the occlusion orifice, and thus the urethra 12, so as to permit material to move therethrough. It will be understood that because of the spring-like memory of the sphincter, when the pressure relief cuff 14 is released, the articulating structure 10 will resume its normal configuration illustrated in FIGS. 1 and 3 so that the urethra is normally held occluded and continent.

From the foregoing, it will be evident that by providing the appropriate elastomeric or resilient polymeric material and by properly molding the same to provide the configuration described in the drawings, relaxing or occluding the lumen, in this case the urethra, can be effected by simply pulling on the pressure relief cuff and subsequently relaxing the pressure relief cuff. In some cases however, the patient will be able to automatically manipulate and control the sphincter by means of intraluminal pressure, such as that generated by biochemical or muscle forces naturally occurring from within the patient's body, thereby permitting the passage of urine, blood, or other intraluminal materials.

Figure 5:
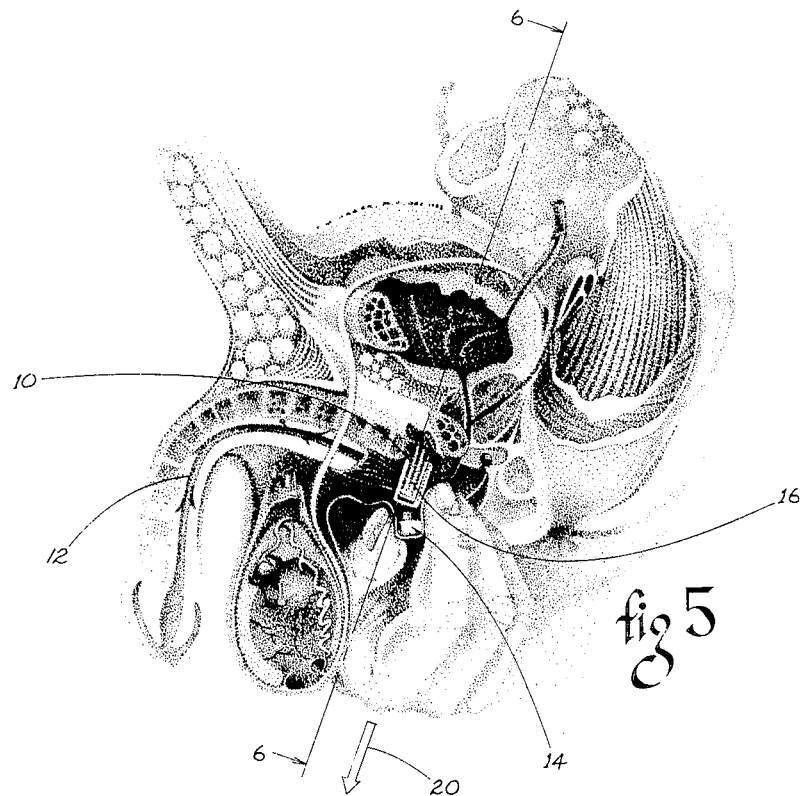
FIG. 5 is a broken away anatomical view of a patient's urethra with the elastomechanical sphincter of this invention in place illustrating how the same is operated.

Referring now to FIG. 5, there is shown a preferred location of the sphincter for occlusion of the urethra and opening of the urethra. As shown in FIG. 5, the articulating structure surrounds the bulbous urethral aspect of the corpus spongiosum with the pressure relief cuff 14 extending below, as described with respect to FIGS. 1 through 4. The pressure cuff lies adjacent to a palpable loose skin area of the patient such as the skin adjacent and anterior to the anal orifice and/or the posterior superior aspect of the scrotum. In FIG. 5, there is shown diagrammatically a person's thumb and index finger pulling downwardly in the direction of the arrow 20 to open the occlusion orifice as described with respect to FIGS. 2 and 4.

Figure 6:
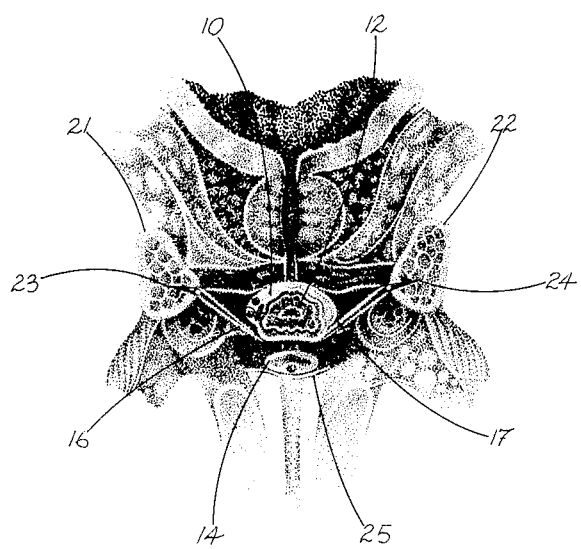
FIG. 6 is a cross section taken in the direction of the arrows 6—6 of FIG. 5.

FIG. 6 illustrates more clearly the manner in which the suture attachment means 16 and 17 are secured to the bone or tissue such as indicated at 21 and 22, this bone preferably constituting the ischium of the pelvis or the tissue constituting the crura of the penis. The actual supporting structure for the attachment thereof can be effected by appropriate orthopedic staples 23 and 24 respectively, as shown in FIG. 6. Also shown in FIG. 6 at 25 is the palpable loose skin area bordering a part of the pressure relief cuff 14. As described heretofore, when the patient manually releases the pressure relief cuff which has been grasped by compressing the loose skin bordering either side of the cuff, the pressure relief cuff will return upwardly as the natural elasticity of the articulating structure closes the elongated occlusion orifice about the urethra.

Referring now to FIG. 7, there again is shown an elastomechanical sphincter similar to that described in FIGS. 1 through 4 but wherein there are included radio opaque spherical telemetry elements 26 embedded in the articulating structure 10 about the elongated occlusion orifice so that all the degree of aperture of the sphincter can be fluoroscopically monitored while in situ. In FIG. 7, the pressure relief cuff 14 is shown somewhat contorted at its bottom, the same being depressed upwardly as at 27. This is the shape that the pressure relief cuff 14 would assume when a person is sitting down, in view of the orientation, in a relatively upright position of the sphincter device, as described in FIGS. 5 and 6. This deformation of the pressure relief cuff 14 into an ellipsoid-shape will result in a slight upward force on the articulating structure 10 serving further to occlude the urethra so that there is provided additional continence safety factor for the patient while in a seated position, without inducing pain through a pressure relief cuff which does not deform and collapse for patient comfort.

In the perspective view of FIG. 8, the sphincter is similar to that described already except that a supporting membrane is not included in the ring-shaped pressure relief cuff. It will be noted that the top of the articulating structure has integral encoding areas 28 for appropriate serialization of the devices and subsequent identification and traceability thereof.

The embodiment of FIG. 8 also shows more clearly an appropriate attachment means for closing the channel 13 after the articulating structure has been positioned about the urethra or other lumen. As shown, this attachment means takes the form of a pair of "U" shaped closure staples 29 and 30 with extending legs each terminating in conical-shaped, rounded protrusions of larger diameter than the legs. With this arrangement, the closure staples can be pressure-inserted into opposite sides of the articulating structure straddling the channel 13, the conical-shaped, rounded protrusions temporarily spreading and stretching the elastomeric polymer material of the articulating structure and the lengths of the closure staple legs being at least equal to the thickness of the articulating structure so that the protrusions extend out the opposite sides of the articulating structure to hold the closure staple legs in place. It will be noted (as illustrated in FIG. 7) that two end protrusions for one of the closure staples are protruding. On the other hand, the U-shaped base of the other staple is shown extending in a parallel and opposite direction.

As is best shown in FIG. 8, a further feature of this invention involves the encapsulating with silicone, polyurethane, or the like, of one or more of the proximal extending ends of the suture attachment means 16 and 17 from the sphincter articulating structure. In this respect, there is provided an intermediate cylindrical terminating shape 31 in the suture attachment means 17 up to which encapsulation takes place as indicated at 32. A similarly terminating cylinder shape 33 is provided in the other suture attachment means 16 and the area between this cylinder and the exit point from the articulating structure is encapsulated in silicone, biomeric polyurethane, or the like, as indicated at 34. This encapsulation stabilizes the suture attachment means and assures complete vulcanization of said suture attachment means to the articulating structure during the molding of the elastomechanical sphincter itself. Said suture attachment means also provide flexible yet non-extensible reinforcement means to strengthen the hingedly manipulable portions of the articulating structure.

FIG. 9 shows a perspective view of a typical fastening means in the form of the closure staple 29 described in FIG. 8 and FIG. 10 is an enlarged fragmentary view of the end of the leg constituting an enlarged portion 35 with a conical rounded shape 36. It will be noted that the diameter of the enlargement 35 is greater than the diameter of the leg so that once the same is forced out the exit opening on one side of the channel 13 in the articulating structure, it will essentially hold itself in place until an exponentially greater force in the opposite direction is applied to facilitate extraction and removal of the closure stable.

According to a second embodiment of the invention and referring to FIGS. 11-14 of the drawings, an elastomechanical sphincter 50 is shown having a unique pressure variation and control system. Sphincter 50 has particular application to a patient having physiological or neurological characteristics which require that additional occlusive forces be occasionally generated to achieve continence above those forces which are available from the previously disclosed sphincter of the first embodiment. Sphincter 50 is fabricated from an elastomeric polymer material, such as silicone or the like, having a spring-like memory. Sphincter 50 comprises an articulating structure 52 having an elongated, normally closed occlusion orifice 53 to embrace a patient's lumen (e.g. urethra) for variably opening and closing the lumen to control the movement of material therethrough. Articulating structure 52 includes upper and lower articulating portions 52-1 and 52-2 which are similar in construction and operation to the articulating halves 10-1 and 10-2 that were previously disclosed while referring to articulating structure 10 of FIGS. 1–8. (However, no limitation of the invention is intended by the designation and orientation of the upper and lower portions of articulating structure 52). Therefore, some of the details of articulating structure 52 will not be repeated herein.

However, unlike the sphincter of FIGS. 1–8, the upper portion 52-1 of articulating structure 52 of sphincter 50 includes a hollow, extensible chamber 54 formed therein (best shown in FIG. 14). As will be disclosed in greater detail hereinafter, chamber 54 is adapted to be filled with a force transmitting medium to cause the inflation thereof and a corresponding closure of occlusion orifice 53 whereby to increase the occlusive pressures generated around the patient's lumen. As is best shown in FIG. 12, the lower portion 52-2 of articulating structure 52 includes a testing appendage 55 coextensively formed and extending outwardly therefrom. Testing appendage 55 has an opening extending therethrough by which to receive a suitable tool or fixture (not shown) for establishing a pressure profile of the sphincter 50 so as to ensure that sufficient occlusive forces to achieve continence will be available after sphincter 50 is implanted in the body of a patient. Moreover, a syringe receiving terminal 56 of solid cross section is coextensively formed with and extended outwardly from the upper portion 52-1 of articulating structure 52. Syringe receiving terminal 56 is positioned to receive therethrough a portion of a syringe during the manufacture of sphincter 50, so as to provide a purging vent when a force transmitting medium is initially introduced into the sphincter (as will also be disclosed in greater detail hereinafter).

Figure 15:
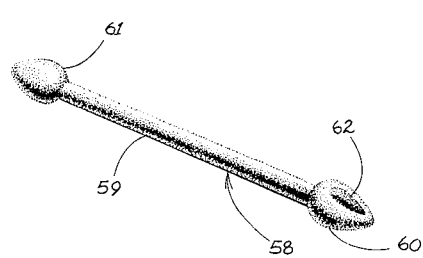
FIG. 15 is a perspective view of a closure pin used in the sphincter embodiment of FIG. 11.

What is more, and as an alternative to the closure staples which were previously disclosed while referring to FIGS. 9 and 10, the articulating structure 52 of sphincter 50 is constructed so as to be secured about the lumen of a patient by means of a closure pin 58. Referring briefly to FIG. 15 of the drawings, closure pin 58 comprises an elongated stem 59 having oppositely disposed end tips 60 and 61. End tips 60 and 61 are conically-shaped, rounded protrusions having a larger diameter than that of the stem 59. A hole 62 is formed through at least one end tip (e.g. 60) of closure pin 58. Hole 62 is suitably sized to receive a tool or fixture (not shown) therein so that pin 60 may be withdrawn from articulating structure 52, whereby to permit the spreading of the upper and lower articulating portions 52-1 and 52-2 to enable occlusion orifice 53 to be either positiond around or removed from around the lumen.

Figure 16:
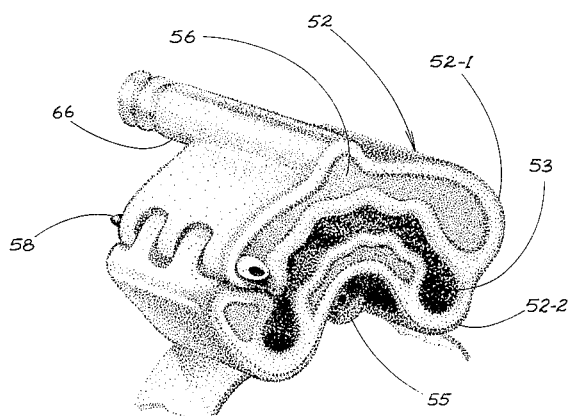
FIG. 16 is a perspective view of the articulating structure of the sphincter of FIG. 11 for explaining the use of the closure pin of FIG. 15.

More particularly (and as best shown in FIG. 16), the upper and lower articulating portions 52-1 and 52-2 are removably connected together in an interlocking relationship by closure pin 58. That is, closure pin 58 is pressure-inserted through alternately extending and interdigitated segments of articulating portions 52-1 and 52-2. The conically shaped end tip 60 or 61 momentarily spreads the elastomeric material of articulating structure 52 to facilitate entry of closure pin 58 therethrough. After the insertion of closure pin 58 through articulating structure 52, each of the end tips 60 and 61 projects outwardly therefrom, so that pin 58 will remain in place until a substantially greater force is applied (by means of the aforementioned tool or fixture at hole 62) to extract pin 58.

Referring once again to FIGS. 11–14, a connecting channel 66 is shown communicating between articulating structure 52 and a reservoir 64 containing a pressure transmitting medium. Connecting channel 66 functions as a conduit to permit the passage of the pressure transmitting medium between reservoir 64 and articulating structure 52. A first end of connecting channel 66 includes a throat 68 which communicates with the chamber 54 at the upper portion 52-1 of articulating structure 52. As is best shown in FIG. 14, throat 68 is coextensively formed with syringe receiving terminal 56 at the upper portion 52-1 of articulating structure 52. Thus, and as earlier explained, when a syringe (not shown) is inserted through terminal 56 (during the manufacture of sphincter 50), the tip of the syringe can also extend into throat 68 for communication with connecting channel 66 and, therefore, reservoir 64. Moreover, and by virtue of both its physical mass as well as the characteristics of the sphincter's elastomeric polymer material, syringe receiving terminal 56 provides a self-sealing means for "healing" a puncture caused by the insertion and withdrawal of a syringe therethrough.

A small channel 70 (best shown in FIG. 14) extends between connecting channel 66 and the chamber 54 at the upper portion 52-1 of articulating structure 52. Therefore, and as will soon be disclosed, a continuous flow path is established by which a force transmitting medium can be conveyed between reservoir 64 and the chamber 54 at the upper portion 52-1 of articulating structure 52 by way of channels 66 and 70.

Connecting channel 66 which, as earlier disclosed, functions as a conduit to permit the passage therethrough of a force transmitting medium, is provided with a plurality of rib-shaped anti-kinking means extending along the length thereof. In a preferred embodiment, the anti-kinking ribs comprise parallel disposed rings 72 molded into the sphincter's elastomeric material around the periphery of channel 66. In the embodiment illustrated, the rings 72 are individually formed around channel 66 in respective planes which are in perpendicular alignment with the longitudinal axis of sphincter 50. However, it is also within the scope of this invention to form the sphincter ribs as a single and continuously winding spiral ring (not shown), the direction of which lies in a plane which is aligned at an angle with the longitudinal axis of channel 66. Rings 72 reduce the chances of kinking or collapsing connecting channel 66, so as to prevent occlusions therein and an undesirable interruption in the passage of the force transmitting medium between reservoir 64 and articulating structure 52.

Figure 17:
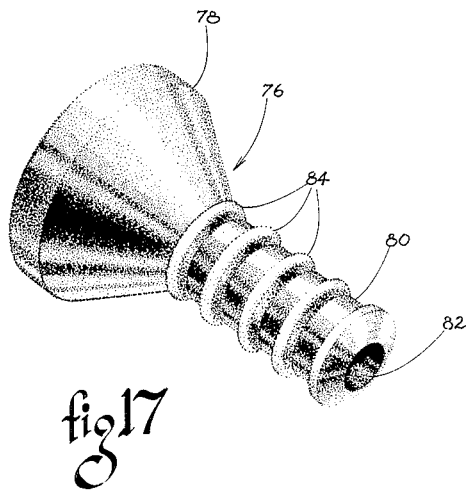
FIGS. 17–19 illustrate the details of an insert used in the sphincter of FIG. 11.
Figure 18:
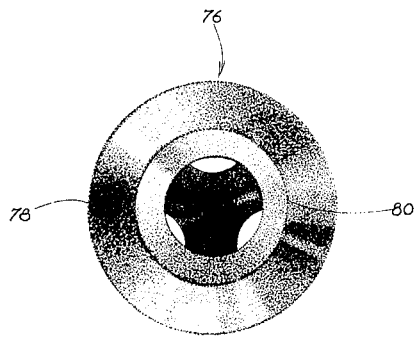
Figure 19:
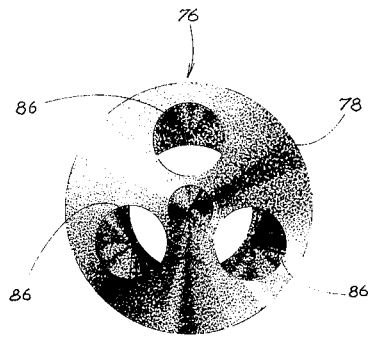

The second end of connecting channel 66 is interfaced with a hollow pressure regulating chamber 74. Located within chamber 74 is an insert 76, the details and advantages of which are now described while referring to FIGS. 17–19 of the drawings. Insert 76 is preferably fabricated from silicone, biomeric polyurethane, titanium, stainless steel, or any other suitable biocompatible, structurally sound and non-corrosive material and comprises a hollow and generally conical base portion 78 and a tubular end portion 80. A channel 82 extends through tubular end portion 80 into the hollow base portion 78. One or more (e.g. three) orifices 86 are formed in the base portion 78 of insert 76, so that a continuous fluid path comprising channel 82 and orifices 86 is established through insert 76. In the embodiment illustrated in FIG. 19, three orifices are uniformly spaced around the base portion 78 of insert 76. However, it is to be understood that any number of orifices may be formed in base portion 78 to communicate at the hollow interior thereof with the channel 82 of tubular end portion 80.

In the assembled sphincter relationship, the conical base portion 78 of insert 76 is located at approximately the center of pressure regulating chamber 74. Thus, pressure regulating chamber 74 is suitably sized to accommodate base portion 78 therein. The tubular end portion 80 of insert 76 is dimensioned so as to be securely received within the second end of connecting channel 66. To promote the positioning of tubular end portion 80 within channel 66, a plurality of parallel disposed and outwardly extending ribs or rings 84 may be formed along the length of end portion 80. Rings 84 are dimensioned so as to be received in an interlocking relationship with the interior concavities of one or more of the anti-kink ribs or rings 72 formed at the second end of connecting channel 66 when sufficient force is exerted to locate the tubular end portion 80 of insert 76 therein during the manufacture of the presently described sphincter 50. Therefore, the insert 76 is securely positioned so as to function, in part, as a structural member, whereby to create a more rigid and relatively non-compressible interface between connecting channel 66 and pressure regulating chamber 74.

Pressure regulating chamber 74 is interconnected with reservoir 64 by way of a short neck 88. A series of vanes 75 (best shown in FIG. 20) are formed (e.g. molded) into the body of pressure regulating chamber 74. Vanes 75 extend between the neck 88 and the base portion 78 of insert 76 to ensure and increase the flow of pressure transmitting medium therebetween. Referring once again to FIGS. 11-14, the longitudinal axes of reservoir 64, neck 88, insert 76 and connecting channel 66 are aligned with one another so that a single continuous passage is formed through sphincter 50 by which the pressure transmitting medium is conveyed between reservoir 64 and the chamber 54 at the upper portion 52-1 of articulating structure 52. This aforementioned passage through sphincter 50 is evacuated of air and/or other gases which may be present during sphincter manufacture so as to ensure complete efficacy of sphincter operation.

Reservoir 64 is initially filled with the pressure transmitting medium, which may be, for example, a gel, a silicone lubricating fluid, iothalamate fluid, a saline hydraulic fluid, or any other suitable low compressibility material. The distal end of reservoir 64 includes closure 89 which may contain polymer-impregnated velour or other reinforcing material for increased resistance to leaks. The reservoir 64 and the end closure 89 thereof include complementary interlocking bands and surfaces which are secured (e.g. vulcanized) together to maximize strength as well as minimize the possibility of leaks at the interface therebetween. During the manufacture of sphincter 50, the pressure transmitting medium is typically introduced to reservoir 64 by means of a syringe which is inserted therein by way of end closure 89 at a syringe receiving port 90. As earlier disclosed, when the tip of a syringe (not shown) is inserted into reservoir 64 at port 90 to supply the reservoir with the pressure transmitting medium during sphincter manufacture, the detached tip of a second syringe with valving to permit only outward flow of pressure transmitting medium (also not shown) is inserted into the throat 68 of connecting channel 66 by way of syringe receiving terminal 56. Thus, the second syringe tip is available to serve as a one way vent for air or other gaseous matter that might undesirably be supplied to the sphincter interior during the filling of reservoir 64.

Referring concurrently to FIGS. 20 and 21' of the drawings, a pressure relief disk 91 is illustrated surrounding the periphery of sphincter 50 at an area adjacent the interface of pressure regulating chamber 74 with neck 88. In the assembled relationship, neck 88 has a circular cross section (best shown in FIG. 20'), the inner diameter of which functions as a valve seat. That is, a flow control means, such as a ball 92, is (e.g. spherically) dimensioned so as to be initially received at the proximal end of neck 88 and at the valve seat thereof, whereby to prevent the passage of pressure transmitting medium between reservoir 64 and articulating structure 52. The flow control ball 92 is typically fabricated from a suitable biocompatible, structurally sound and non-corrosive material, such as silicone, biomeric polyurethane, titanium, stainless steel, or the like, which material is radio opaque (i.e. opaque to radio waves in the X-ray band of the spectrum) relative to the flexible, polymeric sphincter material. Flow control ball 92 may also function as a telemetry element so that the location thereof can be fluoroscopically monitored after implantation in the body of the patient.

The operation of the presently disclosed sphincter embodiment is described while referring concurrently to FIGS. 20, 21' and 25 of the drawings. In order to actuate the articulating structure by which to generate increased occlusive pressures around a patient's lumen and as is best shown in FIG. 25, the reservoir 64 is manually compressed (e.g. by the thumb and index finger of the patient), so as to reduce the volume thereof. The compression of the reservoir 64 forces the pressure transmitting medium outwardly therefrom and into the sphincter neck 88. The force of the pressure transmitting medium causes flow control ball 92 to become unseated from the proximal end or valve seat of neck 88, so that the medium may pass through the vanes 75 formed into the body of pressure regulating chamber 74 and the orifices 86 of insert 76 and into connecting channel 66. The force generated by the pressure transmitting medium causes flow control ball 92 to be moved through pressure regulating chamber 74 until equilibrium of fluid forces is achieved or contact is made with the base portion 78 of insert 76 (shown in phantom and designated by the reference numeral 92-1). Thus, insert 76 also functions as a stop to limit the movement of ball 92 away from its valve seat.

From connecting channel 66, the pressure transmitting medium is supplied via channel 70 to the chamber 54 at the upper portion 52-1 of articulating structure 52. Hence, the upper portion 52-1 of articulating structure 52 functions as an expandable pillow, such that when the chamber 54 thereof is filled with pressure transmitting medium as supplied thereto from reservoir 64, upper portion 52-1 wll swell, whereby to cause the pressure concentrating ridges (designated 12' in FIG. 1) thereof to expand in a direction towards the ridges of lower articulating portion 52-2. Therefore, the swelling of upper articulating portion 52-1 will have the effect of correspondingly narrowing the occlusion orifice of sphincter 50 around the lumen (e.g. urethra) of a patient, so as to inhibit the movement of material therethrough and provide for the urethra to be held occluded and continent.

After reservoir 64 has been compressed, the combined forces of back pressure from the hollow expandable chamber within articulating structure 52 and suction from reservoir 64 causes flow control ball 92 to be reseated on the valve seat at the proximal end of neck 88. Accordingly, the flow of pressure transmitting medium through sphincter 50 is again interrupted by the presence of ball 92 in the flow path between articulating structure 52 and reservoir 64. What is more, both the compressed shape of reservoir 64 and the swollen condition of the expandable chamber of upper articulating portion 52-1 are maintained so as to correspondingly maintain the increased occlusive forces being exerted upon the patient's lumen by the pressure concentrating ridges of the upper and lower articulating portions 52-1 and 52-2.

Occasionally, the patient may experience a return of natural continence, such as may occur during the hours of sleep. A return of continence can be caused by the horizontally coplanar orientation of the patient's kidneys, ureters and bladder during sleep relative to the lumen (e.g. urethra). A corresponding reduction in fluidic head pressure on the urethra may (along with the patient's remaining natural sphincteric function if any) contribute to keeping the patient continent. Therefore, and at such times of temporarily returned continence, it may periodically become advantageous to temporarily reduce additional occlusive pressures being applied to the patient's urethra by the expandable chamber within articulating structure 52 in order to minimize the possibility of ischemia, erosion, and/or necrosis. Moreover, immediately after implantation, or until post-operative edema subsides, the physician may wish to selectively adjust the occlusive pressures being generated by the expandable chamber within articulating structure 52, so that sphincter 50 can be customized to the requirements of the patient.

Accordingly, and referring concurrently to FIGS. 21, 21' and 26 of the drawings, the pressure relief disk 91 may be manually activated, whereby to shrink the chamber 54 at the upper portion 52-1 of articulating structure 52 and thereby maximize circulatory blood (or other material) flow through the lumen (e.g. urethra). More particularly, and as is best shown in FIG. 26, the pressure relief disk 91 is grasped by the user's thumb and index fingers so that equal and opposite forces are applied to cause the disk to move in an upward direction and temporarily assume a bowl-like configuration. The requirement that opposing forces be applied to pressure relief disk 91 reduces the chance that chamber 54 might be unintentionally shrunk due to a sudden impact of disk 91. A deformation of relief disk 91 causes a corresponding stressing of the elastomeric material which forms the valve seat 94 (i.e. at the proximal end of the neck 88) in a direction perpendicular to the longitudinal axis of sphincter 50. That is, and as is best shown in FIG. 21', the original circular cross-section of the neck 88 and the valve seat 94 thereof is changed to a generally elliptical cross section. The elliptical shape of valve seat 94 creates return passages 96 through which pressure transmitting medium can be conveyed by means of suction past the spherical flow control ball 92 (in a direction indicated by reference arrows 98) from articulating structure 52 back to reservoir 64. Moreover, the establishment of return passages 96 in the elliptical valve seat 94 creates a vent by which to equalize the pressure on both sides of the flow control ball (designated 92-1 in the seated position), so as to permit reservoir 64 to expand to its original shape and volume. The regaining of pressure equalization causes flow control ball 92 to be again moved off its seat 94 and into contact with the base portion 78 of insert 76 to maximize the return flow of pressure transmitting medium from articulating structure 52 to reservoir 64 via the neck 88.

As the reservoir 64 begins to fill up with its original supply of pressure transmitting medium, the chamber 54 at upper portion 52-1 of articulating structure 52 correspondingly begins to shrink to its original and unexpanded size. Accordingly, the pressure concentrating ridges of upper articulating portion 52-1 are moved in a direction away from the ridges of the lower articulating portion 52-2 in order to open the occlusion orifice of sphincter 50 and thereby reduce the occlusive pressures being exerted by articulating structure 52 on the patient's lumen.

As a variation 50-1 of the present sphincter embodiment, the insert 76, flow control ball 90 and pressure relief disk 91 associated with pressure regulating chamber 74 may be replaced by a monolithic pressure regulating chamber 100 fabricated from a an elastomeric biomaterial (e.g. silicone) and characterized by one-piece construction. More particularly, and referring to FIGS. 22 and 22' of the drawings, pressure regulating chamber 100 is shown located within sphincter 50-1 between the second end of connecting channel 66 and reservoir 64. Pressure regulating chamber 100 includes one or more pairs of oppositely disposed flow control appendages 102 that are in a normally closed position across the passage between reservoir 64 and connecting channel 66, so as to prevent the movement of pressure transmitting medium therebetween. That is, in the normally closed position of FIG. 22, appendages 102 extend towards and engage one another to prevent communication between reservoir 64 and channel 66. Flow control appendages 102 also include respective arcuately shaped force receiving surfaces 104 which, as will be disclosed in greater detail hereinafter, are adapted to be rotated around one another whereby to cause both a separation of the normally closed flow control appendages 102 and, subsequently, a corresponding alignment and opening of the passage therebetween.

Extending through the pressure regulating chamber 100 between appendages 102 and reservoir 64 is a flexible and hollow force transmitting body 106. Force transmitting body 106 is spaced from the walls of pressure regulating chamber 100 by longitudinally extending flutes 107. The proximal end of body 106 includes a bulbous portion 108 of relatively large diameter. Bulbous portion 108 has a tapering portion which terminates at the interface 110 of flow control appendages 102. Molded into the exterior surface of pressure regulating chamber 100 adjacent the location of the bulbous portion 108 of force transmitting body 106 is a pair of oppositely disposed pressure pads 112. Pressure pads 112 are of suitable size and shape so as to receive the thumb and index finger of the patient or physician and, as will soon be disclosed, perform a similar function to that of the pressure relief disk (91 of FIGS. 20 and 21).

The operation of pressure regulating chamber 100 of sphincter embodiment 50-1 is now described while continuing to refer to FIGS. 22 and 22'. In order to actuate the expandable chamber of the articulating structure (not shown) by which to generate increased occlusive pressures around a patient's lumen, the reservoir 64 is manually compressed so as to reduce the volume thereof. The compression of the reservoir 64 forces the pressure transmitting medium outwardly therefrom and into the bulbous portion 108 of force transmitting body 106. The force of the pressure transmitting medium is transmitted through the bulbous portion 108 and to the taper thereof at the interface 110 between flow control appendages 102. Accordingly, the pressure transmitting medium acts to forceably separate the flow control appendages 102 and thereby establish a passage therebetween to permit the movement of pressure transmitting medium into connecting channel 66 and subsequently to the expandable chamber of the articulating structure and the occlusion orifice thereof in order to apply occlusive pressures to the patient's lumen (e.g. urethra). When the compression of reservoir 64 is terminated so that no additional pressure is being transmitted by the pressure transmitting medium through the force transmitting body 106, the natural tendency of the normally closed flow control appendages 102 to remain closed causes the appendages to again engage and seal against one another to close the passage therebetween and prevent the movement of force transmitting medium therepast.

As previously indicated, the patient may occasionally experience a return of natural continence, such that it may become necessary to periodically reduce the occlusive pressures being applied to the patient's urethra by the articulating structure in order to minimize the possibility of ischemia, erosion, and/or necrosis. Accordingly, and referring to FIGS. 23 and 23', the pressure pads 112 may be manually activated (whereby to shrink the chamber at the upper portion of the articulating structure and thereby maximize blood, or other material, flow through the patient's urethra). More particularly, the pressure pads 112 are grasped by the user's thumb and index finger so that opposite forces are applied to the bulbous portion 108 of force transmitting body 106 in directions which are generally perpendicular to the longitudinal axis of pressure regulating chamber 100. Therefore, flexible pressure regulating chamber 100 and force transmitting body 106 are compressed whereby a corresponding force is generated (in a direction which is generally parallel to the longitudinal axis of chamber 100) from the bulbous portion 108 of force transmitting body 106 to the arcuately shaped force receiving surfaces 104 of respective flow control appendages 102. Accordingly, the flow control appendages 102 are caused to rotate around one another at force receiving surfaces 104 so that the appendages are again separated. More particularly, the rotation of flow control appendages 102 correspondingly moves flutes 107 in a direction (which is transverse to the direction of closure of flow control appendages 102 across channel 66) through the interface 110 of appendages 102 to establish a passage 114 therebetween and permit the movement of pressure transmitting medium from the articulating structure back to the reservoir 64 (in a direction indicated by reference arrows 116). The aforementioned flutes 107 therefore function to prevent the closure of passage 114 under pressure so as to establish passage 114 during the compression of pressure regulating chamber 100. Thus, and as will now be apparent, the inflatable pillow of the articulating structure will shrink and the occlusion orifice thereof will open to reduce the occlusive pressures being applied to the patient's lumen (i.e. urethra) and thereby minimize any interference with the blood flow therethrough. The flexible sphincter 50-1 of FIGS. 23 and 23' is adapted to return to its initial and non-compressed shape of FIGS. 22 and 22' when the hollow chamber of the articulating structure is drained of pressure transmitting medium, reservoir 64 is again filled, and the user releases his grasp of the pressure pads 112.

In FIG. 24, a preferred location is illustrated for the positioning of sphincter 50 in order to occlude and open the patient's lumen (e.g. urethra). The articulating structure 52 of sphincter 50 is shown surrounding the bulbous urethral portions of the corpous spongiosum. However, like the sphincter of the first embodiment, the lumen embraced by articulating structure 52 may also be the intestine, the esophagus, an artery, a vein, or the vas deferins. Suture attachment means (designated 16 and 17 in FIG. 1) are secured to spaced peripheral areas of articulating structure 50 and extended outwardly therefrom for stabilizing connection to adjacent bone or muscle tissue. Connecting channel 66 extends into the patient's scrotum, such that the reservoir 64 of pressure transmitting medium and pressure relief disk 91 are located at a loose skin area at the posterior superior aspect of the scrotum. Thus, the reservoir 64 and pressure relief disk 91 may be suitably located so as to minimize the possibility of any patient discomfort while allowing the patient to manipulate the sphincter 50 in a manner that has been hereinabove described.

From all of the foregoing, it will now be evident that the present invention has provided a greatly improved sphincteric device wherein no pneumatic or hydraulic mediums, tubing prone to kinking and/or leaking, or electrical components are required, nor are any mechanical-type cables interconnecting to components required. The entire structure constitutes essentially a single integral molded part except for the suture attachment means which are molded in place as described so that they can be easily affixed to surrounding bone or tissue during implantation. The described closure staples 29 or pin 58 are easily inserted after the articulating structure and the corresponding elongated occlusion orifice has been positioned about the lumen or urethra.

Changes falling within the scope and spirit of this invention will occur to those skilled in the art. The elastomechanical sphincter is therefore not to be thought of as limited to the specific embodiments set forth herein for illustrative purposes. By way of example, it is also within the scope of the present invention to modify the surface texture (designated 42 in FIG. 8) of the disclosed sphincter to control tissue ingrowth thereon. More particularly, to inhibit fibrous tissue ingrowth, a polished or plated sphincter surface texture is provided. However, to encourage tissue ingrowth onto the sphincter, a porous surface is otherwise provided. Such tissue ingrowth may serve to stabilize the position of the sphincter without the need for the suture attachment means (of FIGS. 7, 8 and 24). Moreover, a temporary suture attachment means, such as polyglycolic acid mesh, may also be employed to temporarily position the sphincter until such adequate tissue ingrowth is experienced as to achieve permanent sphincteric stabilization.

Having set forth the preferred embodiments of the present invention, what is claimed is:

1. A sphincter comprising a prosthetic device suitable for implantation so as to embrace a patient's lumen for occluding and opening the lumen and controlling the movement of material therethrough, said sphincter further comprising:

articulating structure means including an occlusion orifice for surrounding the lumen, at least some of said articulating structure means having a chamber adapted to receive therewithin a pressure transmitting medium for causing said occlusion orifice to close the lumen and inhibit material movement therethrough, reservoir means having a supply of pressure transmitting medium therein, channel means extending between said reservoir means and the chamber of said articulating structure means to permit the pressure transmitting medium to flow therebetween, and normally closed valve means located in said channel means for controlling the passage of pressure transmitting medium between said reservoir means and said articulating structure means, said valve means including at least two arcuate flow control appendages, each of said appendages terminating at an upwardly projecting portion extending within said channel means in a forward direction towards said articulating structure means, said arcuate appendages engaging one another and thereby forming a concave closure across said channel means to prevent the passage of pressure transmitting medium through said valve means in a backward direction towards said reservoir means, and an extensible force transmitting body located between said reservoir means and the interface of said arcuate appendages to receive therein pressure transmitting medium from said reservoir means and thereby cause a separation of said flow control appendages to permit the passage of pressure transmitting medium to said chamber in the forward direction through said valve means.

2. The sphincter recited in claim 1, further comprising manually operable pressure relief means by which to cause a separation of said flow control appendages and thereby open said valve means to permit the removal of pressure transmitting medium from the chamber of said articulating structure means and the opening of both said occlusion orifice and the lumen being surrounded thereby.

3. The sphincter recited in claim 2, wherein said pressure relief means includes at least a pair of oppositely disposed surfaces to which pressure may be manually applied, said pressure surfaces located at the periphery of said sphincter adjacent said force transmitting body so as to be subcutaneously accessible to the patient after implantation of said sphincter, said force transmitting body transferring a force exerted thereon from said pressure surfaces to the interface of said flow control appendages to cause the separation of said appendages and permit the passage of pressure transmitting medium from the chamber of said articulating structure means to said reservoir means.

4. The sphincter recited in claim 3, wherein the transfer of force from said force transmitting body to the interface of said arcuate flow control appendages causes said appendages to rotate around one another, said valve means further including resilient fluted surfaces disposed adjacent the interface of said flow control appendages, the rotation of said arcuate appendages around one another extending said fluted surfaces through said valve means at the interface of said appendages in a direction transverse to the direction of closure thereof in order to cause a separation of said appendages from one another so as to establish a passage therebetween for the communication of pressure transmitting medium in the backward direction through said valve means and from said chamber to said reservoir means.

5. The sphincter recited in claim 1, wherein said articulating structure means includes a pair of articulating portions which are releasably connected together and a closure pin by which to releasably connect said articulating portions together, said closure pin including an elongated stem and oppositely disposed end protrusions which are of larger diameter than the diameter of said stem, said closure pin being of sufficient length so that the end protrusions extend outwardly of said articulating structure means so as to inhibit the removal of said pin therefrom when said pin is inserted through adjacent segments of said articulating portions.

6. The sphincter recited in claim 5, wherein at least one of said end protrusions has a hole extending therethrough so as to be engaged thereat by a means for extracting said closure pin from said articulating portions.

7. The sphincter recited in claim 1, wherein said articulating structure means comprises a pair of oppositely disposed articulating sections hingedly connected together to form said occlusion orifice, one of said articulating sections having formed therein said chamber in which to receive the pressure transmitting medium and the other and opposite of said sections being of substantially solid cross section.

8. The sphincter recited in claim 1, further comprising a plurality of parallel aligned and resilient rings extending along at least some of the periphery of said channel means, said rings reducing the chances of collapsing or kinking said channel means.

9. A sphincter comprising a prosthetic device suitable for implantation so as to embrace a patient's lumen for occluding and opening the lumen and controlling the movement of material therethrough, said sphincter further comprising:

occlusion orifice means for surrounding the lumen, at least some of said occlusion orifice means having an extensible chamber to receive therewithin a fluid medium for causing said occlusion orifice to close the lumen and inhibit material movement therethrough, reservoir means having a supply of fluid medium therein, channel means extending between said reservoir means and the chamber of said occlusion orifice means to permit the pressure transmitting medium to flow therebetween;

valve means located in said channel means for controlling the passage of fluid medium between said reservoir means and the chamber of said occlusion orifice means, said valve means including a flow control ball and a valve seat particularly shaped to removably receive said ball to close said valve means between said reservoir means and said chamber and manually operable pressure relief means by which to unseat said flow control ball and thereby open said valve means in order to permit the removal of fluid medium from the chamber of said occlusion orifice means to permit movement of material through the lumen being surrounded thereby, said pressure relief means communicating with said valve seat to temporarily change the shape thereof and thereby unseat said flow control ball so as to open said valve means and permit the passage of fluid medium therethrough, and an insert having a path extending therethrough to permit the passage of fluid medium between said reservoir means and said occlusion orifice means, said insert including a tubular first end to be received in said channel means and a conical second end extending outwardly of said channel means and communicating with said valve means to limit the movement of said flow control ball off of its valve seat.

10. The sphincter recited in claim 9, wherein said pressure relief means is a flexible disk surrounding at least some of the periphery of said valve seat and positioned so as to be subcutaneously accessible to the patient after the implantation of said sphincter.

* * * * *